United States Patent [19]

Stefas et al.

[11] Patent Number: 5,859,213
[45] Date of Patent: Jan. 12, 1999

[54] AQUEOUS β2'-GLYCOPROTEIN I COMPOSITION

[76] Inventors: Elie Stefas, 94, Allee des Fauvettes, 34280 LA Grande Motte; Marcel Rucheton, 10, rue de la Confrerje; Hubert Graafland, 10 A, Avenue du Professeur Grasset, both of 34000 Montepellier, all of France

[21] Appl. No.: 495,508
[22] PCT Filed: Feb. 9, 1994
[86] PCT No.: PCT/FR94/00143
    § 371 Date: Oct. 23, 1995
    § 102(e) Date: Oct. 23, 1995
[87] PCT Pub. No.: WO94/18228
    PCT Pub. Date: Aug. 18, 1994

[30] Foreign Application Priority Data

Feb. 9, 1993 [FR] France ................... 93 01399

[51] Int. Cl.⁶ ................................... C07K 14/00
[52] U.S. Cl. .................... 530/415; 530/362; 530/363; 530/395; 530/380
[58] Field of Search ................... 530/362, 363, 530/364, 380, 395, 415

[56] References Cited

U.S. PATENT DOCUMENTS 4,289,690  9/1981  Peska et al. .

FOREIGN PATENT DOCUMENTS 2541593  8/1984  France .

OTHER PUBLICATIONS

M. Burstein et al, "Polysulfates, anionic detergents, sodium phosphotungstate and the electrophoretic mobility of plasma proteins", Chemical Abstracts, vol. 89, No. 19, Nov. 1978, Abstract No. 159658, p. 256.

Lozier et al, "Complete amino acid sequence of human plasma beta 2–glycoprotein I", Proceedings of the National Academy of Sciences of USA, vol. 81, Jun. 1984, pp. 3640–3644.

Li et al BiochemJ vol. 267 261–264, 1990.

Sofer etal BioTechniques vol. 1 No. 4 198–203, 1983.

Bonnerjea et al Bio/Technology vol. 4 955–958, 1986.

Medhi et al Gene vol. 108 No. 2 293–298, 1991.

*Primary Examiner*—Sheela Huff
*Assistant Examiner*—Julie E. Reeves
*Attorney, Agent, or Firm*—Cushman Darby & Cushman IP Group of Pillsbury Madison & Sutro LLP

[57] ABSTRACT

A method for preparing an aqueous protein composition from human blood plasma, wherein the plasma undergoes a series of treatments by heating and precipitating agent to give albumin solutions containing the precipitating agent, and said precipitating agent is separated from the resulting solutions to give a crude aqueous albumin solution which is subjected to at least one liquid phase chromatography step to retain at least part of the secondary proteins other than albumin. The chromatography comprises affinity chromatography on a particulate support consisting of neutral particles loaded with at least one compound comprising sulphate groups, whereby, after the albumin solution has been fed through, the particulate affinity chromatography support is eluted by feeding through an aqueous saline solution, preferably by increasing the ionic strength, and the desired protein composition is collected by elution. A protein composition obtained by the method, an isolated glycoprotein having a molecular weight of 50,000±3,000 daltons and contained in the composition, an agent for stabilizing albumin during a Tyndall effect treatment, and an agent for detecting and/or assaying antibodies by ELISA or immuno-imprinting, are also provided.

12 Claims, 2 Drawing Sheets

AQUEOUS β2'-GLYCOPROTEIN I COMPOSITION

This application is a 35 U.S.C. 371 national stage filing of international application PCT/FR94/00143, filed Feb. 2, 1994.

The present invention relates to a protein composition obtained as a secondary product in the production of albumin from human blood plasma, to a method for producing it, to the glycoprotein which it contains and to the use of the said glycoprotein in albumin-stabilizing agents and as an agent for allowing antibodies to be detected and/or assayed.

Figure 1:
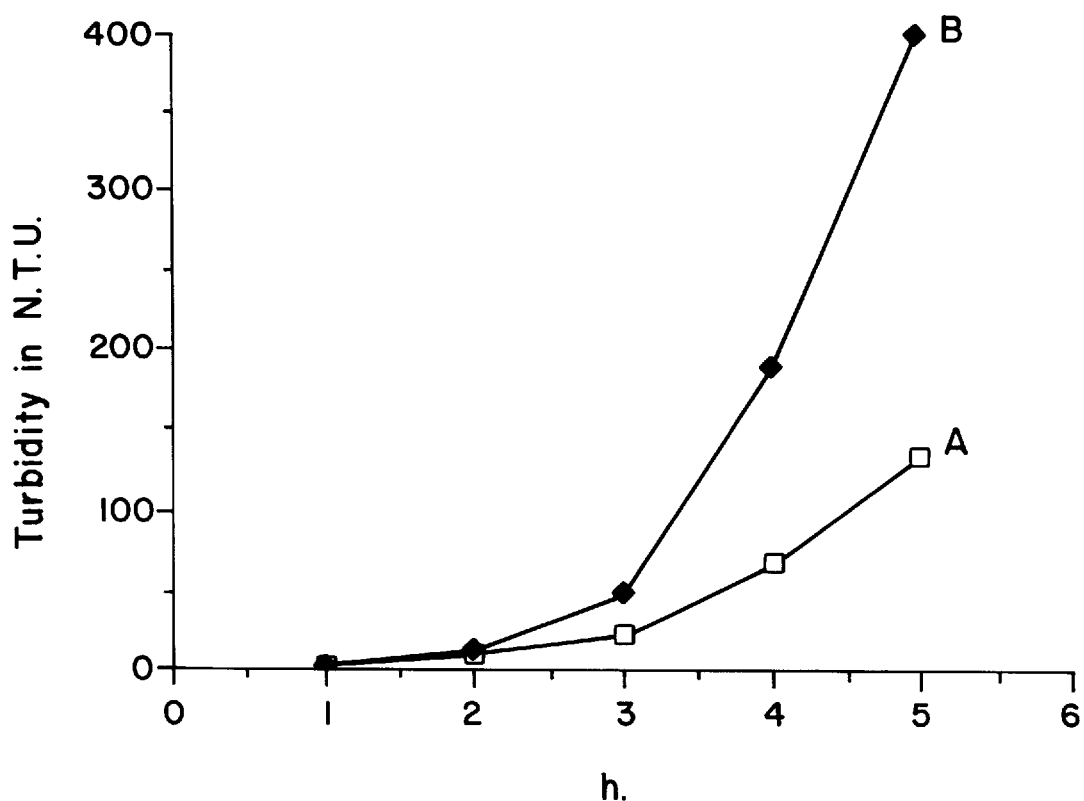
FIG. 1 is a graph that shows the turbidity of the albumin solutions A and B as a function of time.

In the state of the art, it is known that, in order to obtain solutions of human albumin, blood plasma is fractionated either by the Cohn method (see Cohn J. et al., J. Amer. Chem. Soc, 72, 465–474-(1950)), or by a derived method in which successive thermal and ethanolic treatments are carried out or a similar method in which a precipitation agent other than ethanol (especially ether, ammonium sulfate, polyethylene glycol or caprylic acid) is used. According to the Cohn method, which is, in practice, the one used most commonly, the plasma is cooled to −30° C. and then warmed to −2° C., which results in a cryoprecipitate containing anti-hemophilia factor VIII, fibrinogen and fibronectin. The supernatant, referred to as "supernatant I", is separated from the abovementioned precipitate; its pH is lowered to 5.85±0.05 and ethanol is added until the ethanolic concentration is 19% by volume, the temperature being lowered as the ethanol is added, to −5° C. A precipitate is thus obtained, referred to as "precipitate (II+III)", containing in particular the gamma-globulins and a supernatant, referred to as "supernatant (II+III)" containing the albumin and impurities. The supernatant thus obtained is taken up and the alcohol content is increased until an ethanolic concentration of 40% by volume is obtained, the temperature being lowered to about −8° C. A precipitate is thus obtained, referred to as "precipitate IV", and a supernatant, referred to as "supernatant IV", which contains the albumin in a degree of purity of about 94 to 97% by weight. The supernatant IV serves as a starting material for the desired albumin solutions, but it contains a large amount of ethanol; according to a first technique, the supernatant IV may be dialyzed directly against physiological saline, but a very large amount of water then needs to be used and the method is thus slow and expensive; according to another technique, the pH of the supernatant IV is lowered to 4.80±0.05, thereby causing the albumin to precipitate out: this precipitate, referred to as "precipitate V", is separated out and is redissolved in physiological saline, the rest of the ethanol being extracted by dialysis.

The aqueous solutions obtained after dialysis of the "supernatant IV" or of the "precipitate V" which is redissolved contain albumin and about 4% by weight, relative to the total weight of protein material, of other so-called secondary or contaminating proteins and/or polymers.

According to FR-A-2,690,444, the albumin is separated from the other proteins by a liquid phase chromatographic method in which, after dialysis, the aqueous solution containing the albumin is passed through at least one so-called "hydrophobic" chromatography column filled with a particulate material capable of retaining some of the proteins other than the albumin; in order to complete the separation, it is also proposed to pass the aqueous albumin solution through at least one affinity chromatography column containing a neutral particulate support or a particulate support close to neutrality charged with a polysulfated compound. The effluent obtained by this method consists of a solution of purified albumin, the majority of the secondary proteins being bound either to the hydrophobic chromatography column(s) or to the affinity chromatography column(s).

According to a preferred embodiment of this method, an aqueous albumin solution at a pH between 6.5 and 7.8 and at a concentration of greater than 1 g/l and less than 400 g/l is subjected to the chromatography.

A neutral particulate support whose particles are charged with a compound containing. hydrophobic $C_3$–$C_8$ alkyl radicals is advantageously chosen as particulate material capable of retaining the contaminating proteins in the hydrophobic chromatography; a compound containing butyl radicals may in particular be chosen as compound charging the particles of the support: the packing bed consists, for example, of the product marketed by the company "Merck" under the trade name "FRACTOGEL TSK BUTYL-650". The affinity chromatography is preferably performed on dextran sulfate gel. In order to carry out the affinity chromatography and the hydrophobic chromatography, a particulate material having a mean particle size of less than 300 μm is preferably chosen. The chromatography flow rate is generally between 10 and 20 cm/hour and the temperature between 2 and 25° C. The affinity chromatography may be carried out after or, preferably, before the hydrophobic chromatography.

According to the present invention, it has been observed that the secondary proteins bound to the packing beds of the abovementioned chromatography columns could be eluted and useful protein compositions, useful especially in the pharmaceutical field, could thus be obtained.

The first subject of the present invention is consequently a method for obtaining an aqueous protein composition from human blood plasma, in which the plasma is subjected to successive treatments by the action of temperature and by the action of a precipitation agent in order to lead, after at least partial separation of the factors VIII and IX and of the gamma globulins, to albumin solutions containing the precipitation agent, followed by separation, especially by dialysis, of the precipitation agent from the solutions obtained in order to obtain a crude aqueous albumin solution, and the said crude aqueous albumin solution is subjected to at least one liquid phase chromatography in order to retain at least some of the secondary proteins other than the albumin, the said liquid phase chromatography including an affinity chromatography on a particulate support consisting of charged particles of at least one compound containing sulfate groups, characterized in that, after passage of the albumin solution, the particulate support of the abovementioned affinity chromatography [lacuna] is subjected to an elution and in that the desired protein composition is collected on elution.

The elution is preferably carried out by increasing the ionic strength by passage of a saline solution. The saline solution is preferably an NaCl solution, at a concentration at least equal to 0.3M, advantageously of 2M; it is advantageously preceded by a washing operation. The affinity chromatography support is washed in particular using a saline buffer, of molarity equal to 0.16 mol/l, preferably a phosphate buffer consisting of mono- and disodium phosphates, in particular at a concentration of 0.01 mol/l, and of sodium chloride, in particular at a concentration of 0.15 mol/l, in proportions giving a pH of 7.00±0.05. The washing operation is continued for as long as the optical density of the effluent is greater than a predetermined value, for example 0.1 ODU (optical density unit).

The solution obtained by eluting the affinity chromatography column(s) contains a mixture of proteins. Another subject of the present invention is the protein composition thus obtained. This composition contains a glycoprotein which has a molecular weight of 50,000±3000 dalton after or without reduction by 2-mercaptoethanol. The glycoprotein constitutes from 5 to 100% by weight of the total protein content of the composition obtained according to the mode of preparation; the elution generally makes it possible to obtain a weight concentration between 0.05 g and 30 g of glycoprotein per liter of eluate, but this concentration may be reduced by dilution or increased by concentration of the eluate.

The glycoprotein isolated according to the invention has the characteristics and properties given below.

The first 20 amino acids of its N-terminal region have been determined, in particular by gas phase microsequencing using an "Applied Biosystems Inc, model 470" machine coupled to a phenylrheohydantoin analyzer model 120 A (ABI)(SEQ ID NO:1) Gly-Arg-Thr-Cys-Pro-Lys-Pro-Asp-Asp-Leu-Pro-Phe-Ser-Thr-Val-Val-Pro-Leu-Lys-Thr. This sequence of the first 20 amino acids corresponds to that of a plasma β2-glycoprotein described (1) in the article by J. Lozier et al. Proc. Natl. Acad. Sci. ISA Vol. 81, pages 3640–3644, June 1984 and (2) in the article by T. Kristensen et al. FEBS Letters, Vol. 289, 1991, pages 183–186.

The amino acid composition of the glycoprotein isolated according to the invention was determined on two different preparations by two different laboratories:

a) the first preparation A was treated by acidic hydrolysis in 5.7M HCl for 24 hours at 110° C. with a "BECKb) the second preparation B was also analyzed with a "BECKMAN 6300" amino acid analyzer after hydrolysis by 6N HCl for 24 hours and 72 hours.

The results obtained are given in Table I below, where they are compared with the results published by J. Lozier et al. (1) and T. Kristensen et al. (2). These results show that the glycoprotein is a β2'-glycoprotein I similar to the β2-glycoprotein I described by J. Lozier et al. and T. Kristensen et al.

However, this glycoprotein differs from β2-glycoprotein I. Indeed, after purification, precipitation of the glycoprotein according to the invention with acetone and dialysis against distilled water, sequencing results in the identification of 14 amino acids, emerging in pairs, and corresponding to the N-terminal region of the protein. Given the degree of purity of the protein preparation, this corresponds to cleavage of the starting protein. Indeed, 7 of these amino acids correspond to the N-terminal region. The sequence concerned is as follows (SEQ ID NO:2):

Gly-Arg-Thr-Cys-Pro-Lys-Pro The other 7 amino acid, by deduction, correspond to the peptide (SEQ ID NO:3):

Phe-Trp-Lys-Ser-Asp-Ala-Ser This peptide corresponds to the region between amino acids 315 and 321 which has been described by J. Lozier for β2-glycoprotein I but with a difference of one amino acid. This involves a serine in place of a threonine. The glycoprotein isolated according to the invention is thus a β2-glycoprotein I allotype, which will be referred to hereinbelow as β2'-glycoprotein I.

After cleavage of the protein with cyanogen bromide, separation of the peptides obtained and analysis of the first three amino acids in each peptide, the results described by J. Lozier et al. are found.

A second subject of the present invention is thus the protein composition obtained by elution of the affinity chromatography column(s) in the method described above and the β2'-glycoprotein I, as defined above.

TABLE I

| | GLYCOPROTEIN isolated | | | | | β2-GLYCOPROTEIN I | | |
|---|---|---|---|---|---|---|---|---|
| | Preparation A | Preparation B | | | | | | |
| | Hydrolysis 24 H | Hydrolysis 24 H | | Hydrolysis 72 H | | According to (1) | According to (2) | |
| Amino acids | % of number of residues | nmol | % of number of residues | nmol | % of number of residues | % of number of residues | Number of residues/moles of protein | % of number of residues |
| Asp | 9.68 | 6.637 | 8.961 | 6.092 | 9.071 | 8.9 | 28 | 8.723 |
| Thr | 7.89 | 6.000 | 8.101 | 5.574 | 8.299 | 8.3 | 27 | 8.411 |
| Ser | 5.01 | 4.609 | 6.223 | 3.827 | 5.698 | 5.8 | 20 | 6.231 |
| Glu | 8.37 | 6.130 | 8.276 | 5.340 | 7.951 | 7.3 | 24 | 7.477 |
| Gly | 7.62 | 5.550 | 7.493 | 5.382 | 8.014 | 7.1 | 23 | 7.165 |
| Ala | 5.91 | 4.490 | 6.062 | 3.911 | 5.823 | 5.2 | 17 | 5.296 |
| Cys | 1.59 | 3.640 | 4.914 | 3.497 | 5.207 | 6.7 | 22 | 6.854 |
| Val | 5.87 | 3.180 | 4.293 | 3.564 | 5.307 | 5.5 | 17 | 5.296 |
| Met | 1.08 | 0.757 | 1.022 | 0.826 | 1.230 | 1.2 | 4 | 1.246 |
| Ile | 3.95 | 2.275 | 3.072 | 2.618 | 3.898 | 4.0 | 13 | 4.050 |
| Leu | 5.78 | 4.405 | 5.947 | 3.841 | 5.719 | 5.2 | 18 | 5.607 |
| Tyr | 4.38 | 3.440 | 4.644 | 2.682 | 3.993 | 4.3 | 14 | 4.361 |
| Phe | 5.64 | 4.167 | 5.626 | 3.906 | 5.816 | 5.5 | 18 | 5.607 |
| His | 1.65 | 1.350 | 1.823 | 1.090 | 1.623 | 1.5 | 5 | 1.558 |
| Lys | 10.14 | 6.809 | 9.193 | 5.880 | 8.755 | 9.2 | 30 | 9.346 |
| Trp | | | | | | | 5 | |
| Arg | 3.31 | 2.258 | 3.049 | 1.866 | 2.778 | 3.1 | 10 | 3.115 |
| Pro | 12.13 | 8.370 | 11.301 | 7.265 | 10.817 | 9.5 | 31 | 9.657 |

MAN 6300" amino acid analyzer linked to a "GOLD" system for interpretation,

It was found that the protein composition and the β2'-glycoprotein are antigenic, that is to say that they are detected by the ELISA method or by immuno-imprinting, using human antibodies, for example for individuals infected with HBV, HIV or Gougerot-Sjögren syndrome; they are also recognized under certain conditions, in ELISA, by monoclonal antibodies specific for the p 25/p 55 gag of the HIV1 virus (Ac. Mo. RL4.72.1)and for the antioncogenic protein p 53 (Ac. Mo. 122); the composition and β2'-glycoprotein I may thus be used for the characterization and assay of antibodies against this protein in patients suffering from AIDS, hepatitis B, leukemias, Gougerot-Sjögren syndrome or myelomas. The ELISA method is described, for example, in the article by Engvall et al. Immunochemistry 1971, 8, pages 871 to 879 and the immuno-imprinting method is described, for example, by Towbin et al. Proc. Natl. Acad. Sci. USA, 1979, 76, pages 4350–4354.

The protein composition and β2'-glycoprotein I inhibit the denaturation of albumin at 60° C. observed in turbidimetry, in a "dose-dependent" manner; it is thus possible to use it [sic] in order to stabilize albumin, especially during tyndallization.

β2'-Glycoprotein I may be separated from the secondary proteins with which it is mixed in the protein composition obtained by elution of the affinity chromatography column, in the manner described below: the composition is eluted from dextran sulfate gel by an NaCl solution at least equal to 0.3M, advantageously in the region of 2 mol per liter; the eluate obtained is diluted in saline buffer so as to lower its ionic strength to less than 0.2; the solution obtained is subjected to a chromatography on phosphate gel, and the glycoprotein bound to the phosphate gel is then eluted by increasing the ionic strength with a saline buffer preferably having an ionic strength of greater than 0.4. The flow rate of the phosphate gel chromatography is preferably between 10 and 20 cm/hour and the temperature is preferably between 0 and 40° C., preferably 2 and 25° C., under usual conditions.

Another subject of the invention is an agent for stabilizing albumin during tyndallization, containing the protein composition or the β2'-glycoprotein I defined above and an agent which makes it possible to detect and/or assay antibodies from humans infected with HBV, HIV, Gougerot-Sjogren syndrome or myelomas, by the ELISA method or by immuno-imprinting, characterized in that it contains the protein composition or the β2'-glycoprotein I defined above.

In order to gain a better understanding of the invention, a mode of preparation of the β2'-glycoprotein I according to the invention will be described below, by way of example which is purely illustrative and nonlimiting.

The starting material used is a human plasma fractionated according to the method described by Kistler and Nitschman (Vox Sang. 7, 414–424 (1962)), which is a method derived from that of Cohn, the starting fractions containing the albumin being either the supernatant IV or the precipitate V.

When starting with the supernatant IV, which comprises 40% (by volume) of ethanol and which has a pH of 5.85±0.05, the supernatant is diluted by half with a 7 g/l solution of NaCl. The pH is adjusted to 7.45±0.05 with 1N sodium hydroxide solution. The albumin is preconcentrated to 90 g/l in an ultrafiltration cassette of "Omega" type (Filtron) used in a "Minisette SS Cell NPT Cell" ultrafiltration system (Filtron Techn. Corp.). This cassette has a 0.07 m$^2$ filtering surface area and a retention threshold of 30 KDa. Circulation is provided by a peristaltic pump at a pressure which varies from $2\times10^5$ Pa at the start of the operation to $5\times10^5$ Pa towards the end. When an albumin concentration of 90 g/l has been reached, a 9 g/l solution of NaCl is added to the albumin solution and the dialysis is continued at constant volume until an ethanol content of less than 0.1% by volume is obtained. When the ethanol has been thus removed, the dialysis is continued by concentrating the solution to 200 g of albumin per liter. The pH is adjusted to 7.10±0.05 with 1N hydrochloric acid solution.

When starting with the precipitate V, the said precipitate is resuspended in physiological saline (NaCl solution at a concentration of 9 g per liter) using 4 liters of physiological saline per kilogram of precipitate. Filtration is carried out in order to remove lumps of precipitate which have not been resuspended during stirring; the pH is adjusted to 7.45±0.05 with 1N sodium hydroxide solution and the solution thus obtained is concentrated to 90 g of proteins per liter using the same dialysis system as described before for the supernatant IV. The dialysis is then continued by adding physiological saline and working at constant volume until a final ethanol content of less than 0.1% by volume is obtained. When the ethanol has been thus removed, the dialysis is continued in order to concentrate the solution to about 200 g of proteins per liter. The pH is adjusted to 7.10±0.05 with 1N hydrochloric acid solution.

The albumin solution thus prepared from the supernatant IV or from the precipitate V then undergoes sterile filtration ("Millex-GS" 0.2 micron filter (Millipore)).

The crude aqueous albumin solution obtained first undergoes an affinity chromatography. This chromatography is performed in a 50 ml column (2.5 cm×10 cm) (Biorad), filled with a particulate material sold by the company "Sigma" under the trade name "DEXTRAN BEADS SULFATED". The column is pre-equilibrated by passing 3 column-volumes of physiological saline through the bed. The albumin solution is then put on this column and the effluent may be recovered for the production of albumin.

The progress of the chromatography is monitored by measuring the optical density at 280 nm of the fractions leaving the column. The column flow rate is 16 cm/hour; the chromatography is carried out between 20 and 25° C.

After passage of the albumin recovered as effluent, the affinity column is washed with a saline buffer, close to isotonicity, preferably a buffer consisting of mono- and disodium phosphates, in particular at a concentration of 0.01 mol/l, and of sodium chloride, in particular at a concentration of 0.15 mol/l, having a pH of 7.00±0.05, until the optical density of the effluent is less than 0.1. The proteins bound to the affinity column are then eluted, by increasing the ionic strength, by passage of 2M NaCl solution. The washing operation and the elution are carried out at room temperature, the washing and elution flow rates being 16 cm/h.

SDS-Page denaturing electrophoresis was carried out on the solution obtained. The presence was observed of a diffuse band corresponding to the presence of a protein having a molecular weight of 50,000±3000 daltons after or without reduction by 2-mercaptoethanol. The Schiff coloration technique shows that this protein is a glycoprotein. After coloration of the gel with Coomassie blue, in this experiment, study of the surface area of the optical density peaks shows that the composition contains 55% by weight of β2'-glycoprotein I relative to the total proteins.

The β2'-glycoprotein I is then separated out and purified in the following way: the protein composition obtained by elution of the affinity chromatography column(s) using a saline solution of NaCl at a concentration of 2 mol/liter, is diluted 10 times in a buffer consisting of mono- and disodium phosphates, in particular at a concentration of 0.01 mol/liter, in proportions giving a pH of 6.8±0.05. It then undergoes a chromatography on phosphate gel. This chromatography is performed in a 50 ml column (2.5 cm×10 cm)

(Biorad), charged with a particulate material sold by the company "Bio-Rad" under the trade name "BIO-GEL HTP". The column is preequilibrated by passing through the bed 3 column-volumes of buffer consisting of mono- and disodium phosphates, in particular at a concentration of 0.01 mol/liter, in proportions giving a pH of 6.8±0.05. The protein eluate of the above chromatography, once diluted, is then put on this column. The chromatography is carried out with a flow rate of about 15 cm/hour at a temperature of 20° C. The effluent is removed and the chromatographic support is then washed using a phosphate buffer identical to that which served to equilibrate the column. The washing operation is continued for as long as the optical density of the effluent is greater than a predetermined value, for example 0.1 ODU (optical density unit).

The β2'-glycoprotein I which, under these conditions, binds to the phosphate gel, is then eluted by increasing the ionic strength. The elution operation is preferably performed using a KCl solution having a concentration in the region of 1M. This elution solution consists of mono- and disodium phosphates, in particular at a concentration of 0.01 mol/liter, in proportions giving a pH of 6.8±0.05 and of 1 mol/liter KCl. The progress of the chromatography is monitored by measuring the optical density at 280 nm of the fractions leaving the column. The flow rate for equilibrating, loading, washing and eluting the column is 16 cm/h. The chromatography is carried out at 20° C.

The eluate is recovered and then dialyzed, preferably in an isotonic buffer. By monitoring the progress of the chromatography, it is observed that at least 0.5 g of β2'-glycoprotein I can be loaded per liter of chromatography bed.

The eluate obtained from the hydroxyapatite gel (BIO-GEL HTP) was analyzed by SDS-Page denaturing electrophoresis. The presence of a single band was observed, corresponding to the presence of a protein having a molecular weight of 50,000±3000 daltons, after or without reduction by 2-mercaptoethanol. The purity of this preparation was tested on so-called "HPLC" chromatography on "FRACTOGEL TSK 3000 SW" (Tosho machine) and the presence of a single protein peak is also observed.

The glycoprotein thus isolated has the sequence and composition characteristics mentioned above in the present description, which show that this is a β2-glycoprotein I allotype: β2'-glycoprotein I.

The examples given below show the stabilization of albumin by the composition containing β2'-glycoprotein I.

EXAMPLE 1

Two albumin solutions, A and B, are prepared, of the same protein concentration (90 mg/ml), of the same pH (7.1) and of the same ionic strength. Solution A is an albumin solution obtained according to the process described above but which has not undergone chromatography treatment, and solution B is the solution of purified albumin obtained after affinity chromatography on a dextran sulfate gel in order to remove in particular the protein composition retained on the chromatography column. These two albumin solutions A and B are incubated at 60° C. Hourly, and for 5 hours during the incubation, the turbidity of each solution is measured using a RATIO XR tubidimeter (HACH 43900).

FIG. 1, of turbidity as a function of time, shows a turbidity, due to heat, which is greater for the albumin solution B than for the albumin solution A, thereby indicating that an inhibitor of heat-induced protein denaturation has been removed from the albumin A by means of the chromatographic steps.

EXAMPLE 2

Figure 2:
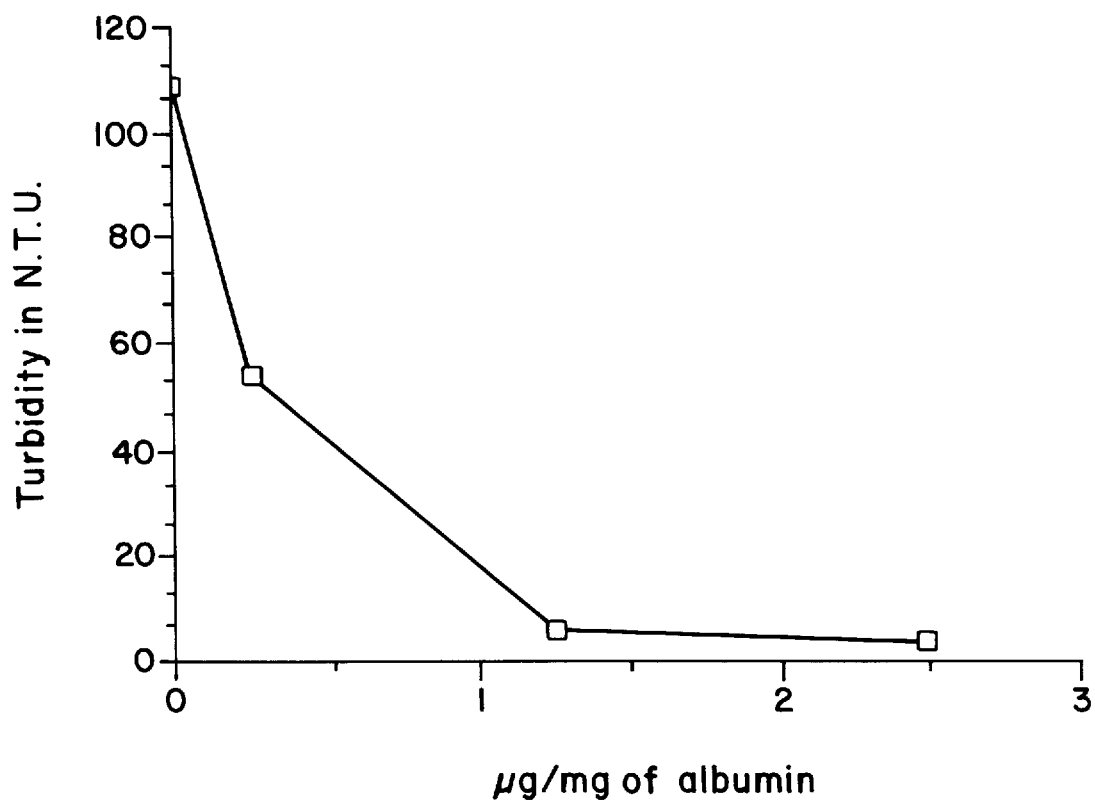
FIG. 2 is a graph that shows as the protein concentrations increases, the turbidity of albumin decreases.

Increasing quantities of eluate from the affinity chromatography on dextran sulfate constituting the protein composition are added to the albumin solution B described in the above example, which has a protein concentration of 70 mg/ml. FIG. 2 shows that when the concentration of this eluate increases, the turbidity of the albumin decreases after heating for 5 hours at 60° C. This curve demonstrates, on the one hand, that the protein composition acts as a tyndallization inhibitor and, on the other hand, that this inhibition is dose-dependent.

---

We claim:

1. A method for obtaining an aqueous glycoprotein composition containing β2'-glycoprotein I from human plasma, said method comprising
   i) alternately cooling and heating said plasma to obtain a first precipitate containing antihemophiliac factor VIII, fibrinogen and fibronectin and a supernatant;
   ii) separating the supernatant from said first precipitate and acidifying the supernatant;
   iii) adding a precipitation agent to the supernatant while cooling to obtain an aqueous albumin solution and a second precipitate containing gammaglobulin;
   iv) separating said aqueous albumin solution from said second precipitate and from said precipitation agent;
   v) subjecting said aqueous albumin solution to affinity chromatography on a particulate support consisting of charged neutral particles, wherein at least one compound in said particles contains a sulfate group, so that said glycoprotein is bound to said particles and albumin remains in solution; and
   vi) eluting said particulate support to obtain an aqueous glycoprotein composition containing β2'-glycoprotein I.

2. The method according to claim 1 wherein elution is accomplished by passage of a saline solution of increasing ionic strength over said particulate support.

3. The method according to claim 2 wherein said saline solution is an NaCl solution.

4. The method according to claim 2 wherein elution is preceded by at least one washing operation.

5. The method according to claim 4 wherein the washing operation is carried out using a saline buffer substantially isotonic to human plasma, in proportions such that the pH is 7.00±0.05 during the washing operation.

6. An aqueous glycoprotein composition obtained by the method of claim 1.

7. The composition of claim 6 having the property of stabilization of albumin during its tyndalization.

8. A composition for the detection or assay of antibodies from humans suffering from hepatitis B virus, human immunodeficiency virus, Gougerot-Sjogren syndrome or myelomas using ELISA or immunoimprinting, comprising the glycoprotein composition of claim 6.

9. β2'-glycoprotein I contained in the aqueous protein composition according to claim 1, having a molecular weight of 50,000±3000 daltons as determined by SDS gel electrophoresis, after or without reduction by 2-mercaptoethanol, in which the first 20 amino acids of the N-terminal region are as follows: Gly-Arg-Thr-Cys-Pro-Lys-Pro-Asp-Asp-Leu-Pro-Phe-Ser-Thr-Val-Val-Pro-Leu-Lys-Thr- (SEQ ID NO:1) and the sequence of amino acids 315 to 321 is Phe-Trp-Lys-Ser-Asp-Ala-Ser (SEQ ID NO:3).

10. The composition according to claim 6 comprising from 5 to 100% by weight of a glycoprotein relative to the total protein content said glycoprotein having a molecular weight of 50,000±3000 daltons as determined by SDS gel electrophoresis after or without reduction by 2-mercaptoethanol, in which the first 20 amino acids of the Nterminal region are as follows: Gly-Arg-Thr-Cys-Pro-Lys-Pro-Asp-Asp-Leu-Pro-Phe-Ser-Thr-Val-Val-Pro-Leu-Lys-Thr- (SEQ ID NO:1) and the sequence of amino acids 315 to 321 is Phe-Trp-Lys-Ser-Asp-Ala-Ser (SEQ ID NO:3).

11. The method according to claim 1 having the further steps of
   vii) treating the aqueous glycoprotein composition of step vi on dextran sulfate by an NaCl solution with a concentration of at least 0.3M per liter to obtain an eluate;
   viii) diluting the eluate obtained with a saline buffer so as to lower its ionic strength to at most 0.2;
   ix) subjecting the eluate to chromatography on phosphate gel; and
   x) adding a saline buffer of ionic strength greater than 0.4 to the chromatography solution to increase the ionic strength, thereby eluting glycoprotein bound to the phosphate gel.

12. The method according to claim 11 wherein the chromatography of steps ix and x has a flow rate between 10 and 20 cm/hour and the temperature during chromatography is between 0° C. and 40° C.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 20 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

```
Gly  Arg  Thr  Cys  Pro  Lys  Pro  Asp  Asp  Leu  Pro  Phe  Ser  Thr  Val  Val
1                   5                        10                            15
Pro  Leu  Lys  Thr
                20
```

( 2 ) INFORMATION FOR SEQ ID NO:2:

```
( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:2:

Gly  Arg  Thr  Cys  Pro  Lys  Pro
1                    5

( 2 ) INFORMATION FOR SEQ ID NO:3:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Phe  Trp  Lys  Ser  Asp  Ala  Ser
    1                    5
```